United States Patent
Chang (10) Patent No.: US 6,661,011 B2
(45) Date of Patent: Dec. 9, 2003

(54) MULTI-COMPONENT GAS ANALYZER HAVING CASSETTE-TYPE LIGHT PATH SYSTEM

(75) Inventor: Shih-Yi Chang, Hsinchu (TW)

(73) Assignee: Oriental System Technology, Hsinchu (TW)

( * ) Notice: Subject to any disclaimer, the term of this patent is extended or adjusted under 35 U.S.C. 154(b) by 182 days.

(21) Appl. No.: 09/893,652

(22) Filed: Jun. 29, 2001

(65) Prior Publication Data

US 2002/0139934 A1 Oct. 3, 2002

(30) Foreign Application Priority Data

Mar. 30, 2001 (TW) .................................. 90107820 A (51) Int. Cl.[7] .............................................. G01N 21/61
(52) U.S. Cl. ..................................................... 250/343
(58) Field of Search ........................................ 250/343

(56) References Cited

U.S. PATENT DOCUMENTS

| | | | |
|---|---|---|---|
| 3,194,111 A | * | 7/1965 | Saunders .................... 250/343 |
| 4,914,719 A | | 4/1990 | Conlon et al. |
| 5,220,402 A | * | 6/1993 | Harvey ........................ 356/246 |
| 5,222,389 A | | 6/1993 | Wong |
| 5,550,375 A | * | 8/1996 | Peters et al. ................. 250/343 |
| 5,734,165 A | * | 3/1998 | Unal et al. ................... 250/343 |
| 5,773,828 A | | 6/1998 | Akiyama et al. |
| 6,121,617 A | * | 9/2000 | Hirayama et al. ........... 250/343 |

* cited by examiner

Primary Examiner—Constantine Hannaher
(74) Attorney, Agent, or Firm—Birch, Stewart, Kolasch & Birch, LLP (57) ABSTRACT

A multi-component gas analyzer includes a light source system, a cassette-type light path system, an optical folding system, and an infrared detecting system. The light source system has an infrared light source and a reflector for providing a parallel infrared light beam. The cassette-type light path system has a cassette, an optical absorption chamber, and a set of concave mirrors. A vent hole set is provided having a plurality of vent holes enclosed by an O-ring for sealing the gas between the stacked-up cassettes. The optical absorption chamber includes a highly reflective coating film coated on the inner wall surface thereof that is employed for introducing the gases to be analyzed and provides a space for contact between the gases and the infrared light.

16 Claims, 11 Drawing Sheets

MULTI-COMPONENT GAS ANALYZER HAVING CASSETTE-TYPE LIGHT PATH SYSTEM

FIELD OF THE INVENTION

The invention relates to a multi-component gas analyzer having cassette-type light path system, and more particularly, relates to a unified and systemized gas analyzer that can analyze multi-component gases at the same time without any movable parts.

BACKGROUND OF THE INVENTION

The health problems, affected by modern living environment of human being and caused by the air pollution resulted from industrialization and dense population, have called wide attention in all walk of life. There are problems of how to analyze and judge the air quality, to what extent of the air is polluted, what kinds of air components are noxious to the health of human being, what the percentage of noxious gas components contained in the air. These problems depend on reliable and precise apparatus to analyze and to measure. Owing to the regulations and air pollution policies imposed by the government at all levels, relatively high demands are requested on the indoor and outdoor air quality as well as on the single and multi-component gas analyzers for analyzing and measuring the exhaust gases of automobiles and motorcycles. In general, the mandate gas components needed to be analyzed and measured are carbon dioxide ($CO_2$), hydrocarbon (HC), and carbon mono-oxide (CO) etc. There are many ways of analyzing and measuring the gas components among the many gas analyzers, and currently, a non-dispersive infrared (NDIR) spectrometry is considered to be the most popular one.

Figure 1:
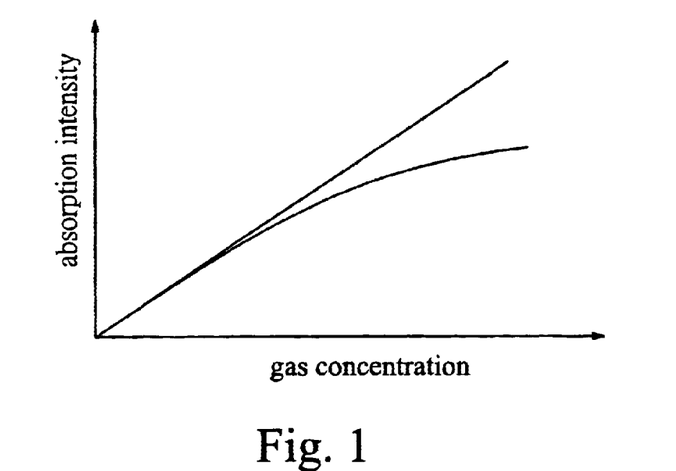
FIG. 1 shows the linear and the non-linear curves for the relationship of the absorbance to infrared versus the concentration of the gas components according to the Beer-Lambert Law.

NDIR is an optical absorption method based on the spectral selected principle. Basically, each kind of gas has one or multiple different Infrared (IR) absorption characteristics. In other word, the IR absorbance for each gas having a specific wave-length relates directly to the concentration of the gas. This kind of IR absorbance principle for a gas is called Beer-Lambert Law. As shown in FIG. 1, the IR absorbance for a gas is proportional to the concentration and the length of light path of the gas and is shown by the following formula $$A = K \times C \times L$$

Where
- A=IR absorbance that takes the logarithm of the ratio of the light intensity of the original incident light to the light intensity after the light is absorbed;
- K=the IR absorption coefficient of the gas;
- C=the concentration of the gas;
- L=the length of light path through which the gas absorbs the IR.

As shown in FIG. 1, while ideally, the absorbance of the gas to IR is linearly proportional to the concentration of the gas, in reality, there is always a discrepancy, thereby, a nonlinear relationship exist between them. Moreover, the higher the optical density, the higher the extent of the discrepancy will be. The optical density denotes the product (C×L) of the gas concentration C and the length of the light path L. To lower the discrepancy so as to improve the measuring accuracy of the system, the designer of the system needs to select an optimum optical density. In other word, a gas having relatively high concentration or high absorbance needs to select a gas analyzer with relatively short light path, and vice versa. Consequently, the design of a gas analyzer that is capable of measuring multi-gas requires that the gas analyzer can select to use a multiple of lengths of light path so as to extend the measurable dynamic range of the apparatus.

Moreover, the frequency range of a specific gas is a constant value, thereby, a specific filter corresponding to the frequency range is required in order to filter and select an IR of a single specific frequency. Thereafter, a sensor is used to sense the variation of the light intensity of the IR. There is also a design option to have a detector combining sensors with filters.

Figure 2:
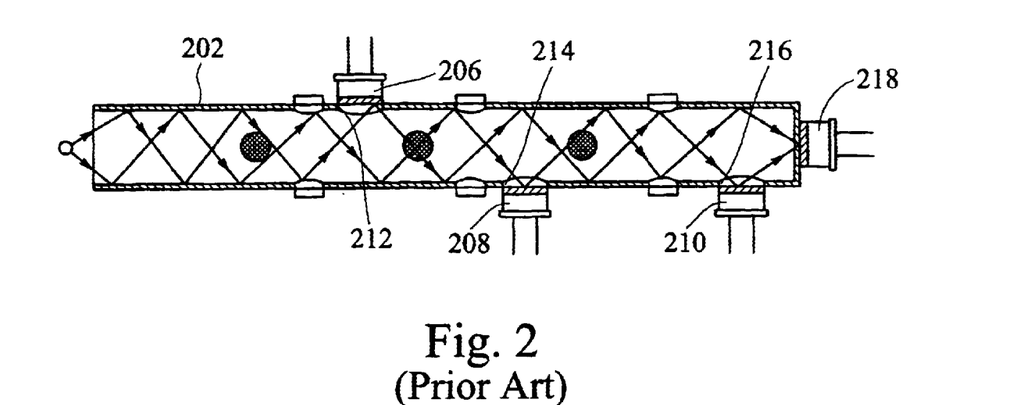
FIG. 2 is a schematic drawing showing the structure of a multi-channel gas sample chamber and the transmittal of infrared in the gas sample chamber according to the first prior art disclosed by the U.S. Pat. No. 5,222,389.

The first prior art quoted by the invention is a multi-channel gas sample chamber disclosed by the U.S. Pat. No. 5,222,389. As shown in FIG. 2, the characteristic of the first prior art is that a plurality of detectors 206, 208, and 210 are provided respectively at their detector ports 212, 214, and 216 on the circumference 202 of a long cylindrical hollow light tube. In addition, a detector 218 is also provided at the end of the light exit. These detectors are used for measuring the multi-gas in response to the above-mentioned principle, that is, a gas having relatively high absorbance to IR needs to select a gas analyzer with relatively short light path. On the contrary, a gas having relatively low absorbance to IR needs to select a gas analyzer with relatively long light path.

However, the first prior art is unable to substantially attain the expected effect for the following reasons:

1. The IR, denoted by arrow heads as shown in FIG. 2, received at the detector 206 208 and 210 that are provided on the circumference 202 of the light tube are incident lights at skew angles rather than at right angles. Since optimum effect of gas measuring can be obtained if the incident lights are at right angles, thereby, the incident IR lights at skew angle will affect the accuracy of the output frequency of the filters in the detectors.
2. Since the incident lights transmitted into the detectors are at skew angles, the intensity of the incident lights is attenuated, consequently, the output signal/noise ratio is lower.

Figure 3:
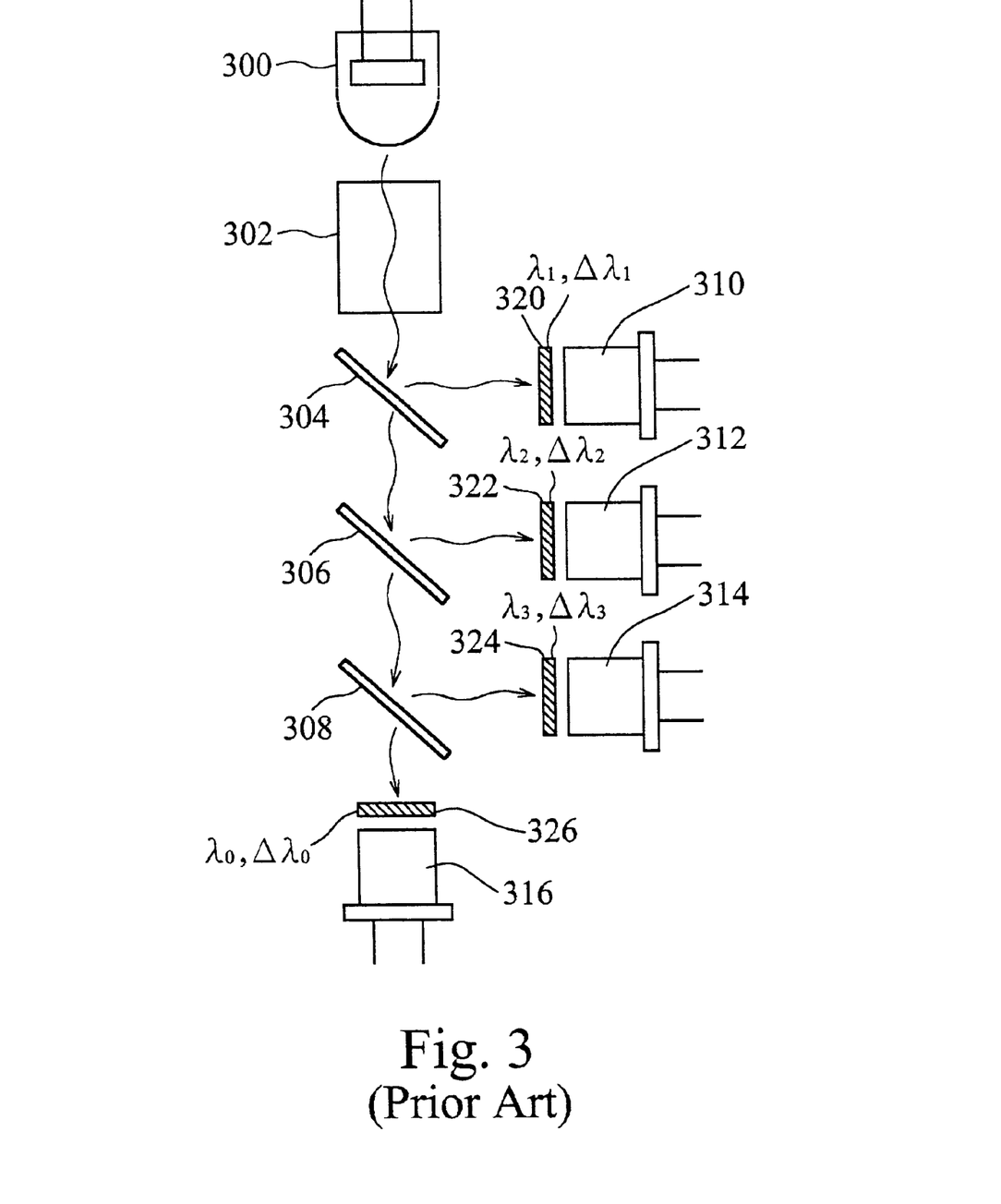
FIG. 3 is a schematic drawing showing the structure of a multi-component gas analyzer and the transmittal of infrared in the multi-component gas analyzer according to the second prior art disclosed by the U.S. Pat. No. 4,914,719.

The second prior art quoted by the invention is a multiple component gas analyzer disclosed by the U.S. Pat. No. 4,914,719. As shown in FIG. 3, the multiple component gas analyzer includes an IR source 300 that can generate light beam; an optical absorption chamber 302; three beam splitter 304, 306, 308; four detectors 310, 312, 314, 316; four filters 320, 322, 324, 326. The light beam transmits through the optical absorption chamber 302, and is then guided into the splitters 320, 322, 324, 326 to become split light beams that are reflected by the splitters 320, 322, 324, 326 and are deflected to the detectors 310, 312, 314, 316. One of the light beams that transmits directly all the way through the series of splitters 320 322, 324, 326 hits into the detector 316 through the filter 326. Each of the filters 320, 322, 324, and 326 corresponds respectively to a specific distinctive frequency range.

However, the second prior art can not substantially attain the effect of extending the measurable dynamic range of the apparatus. Since the length of the optical absorption chamber 302 is the only length that is available, there are no multiple lengths of light path to be selected in order to match the different gas concentration. Here are some of the examples showing the resulting situations.

1. According to the Beer-Lambert Law, the absorption intensity of the gas to the IR will be rather high if a relatively long light path is employed by a relatively high concentration of gas. This will result in the fact that the absorption of the gas to the IR is apt to attain saturation which makes the light intensity measured by the sensor rather weak.

2. On the other hand, according to the Beer-Lambert Law, the absorption intensity of the gas to the IR will be rather low if a relatively short light path is employed by a relatively low concentration of gas. This will result in the fact that the absorption of the gas to the IR is little which makes the variation of the light intensity measured by the sensor is rather limited. Consequently, the detecting ability of the analyzer is relatively low, 3. The above-mentioned extreme cases will result in the fact that the concentration range that can be measured by the gas analyzer is limited. In other word, a gas analyzer having relatively short light path and is adequate for measuring gases having relatively high concentration will make the range of measuring gases having relatively low concentration become narrow. On the contrary, a gas analyzer having relatively long light path and is adequate for measuring gases having relatively low concentration will make the range of measuring gases having relatively high concentration become narrow too.

Figure 4A:
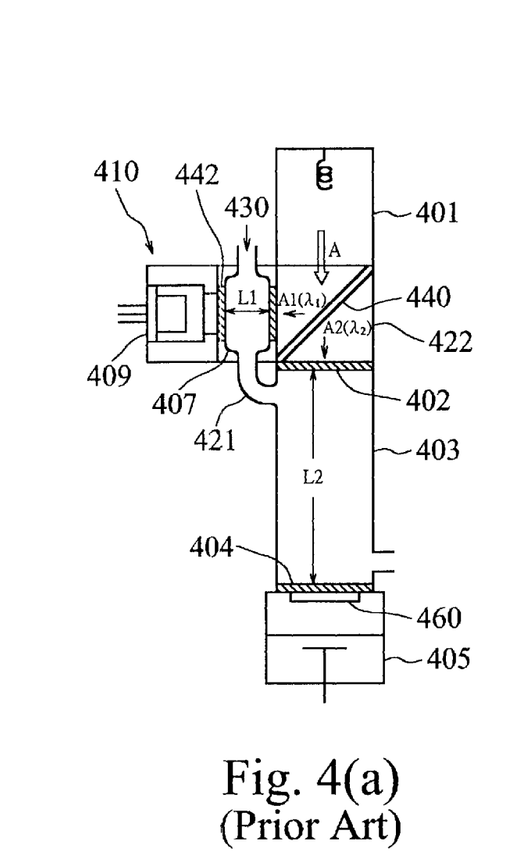
FIGS. 4(a), 4(b), 4(c) are schematic drawings showing the structures of multi-component gas analyzers in three different embodiments respectively according to the third prior art disclosed by the U.S. Pat. No. 5,773,828.

The third prior art quoted by the invention is a gas analyzer disclosed by the U.S. Pat. No. 5,773,828. As shown in FIG. 4(a), one of the embodiments of the third prior art is a two-component measuring gas analyzer. The gas analyzer has a $NO_x$ gas measuring cell 403 having a length L2 of around 60 mm that is connected through a communication part 421 to a $CO_2$ gas measuring cell 407 having a length L1 of around 1 mm. A filter 440, which is provided near the light source 401 and used in a apparatus for transmitting and reflecting the light, is employed to spectrally diffracting a specific wave length of IR. An IR A, originated from the light source and with its specific wave length $\lambda 2$, transmits through a band pass filter 440 to become A2, and with its another wave length $\lambda 1$, reflects from the band pass filter 440 to become A1. A $NO_x$ detector 405 is provided at an end of the gas measuring cell 403 while a $CO_2$ detector 409 is provided at an end of the gas measuring cell 407. By the use of this apparatus, two different gases $NO_x$ and $CO_2$ can be measured by the two mutually connected gas measuring cells 403 and 407 which have different lengths L2 and L1 respectively, through a communication part 421.

Figure 4B:
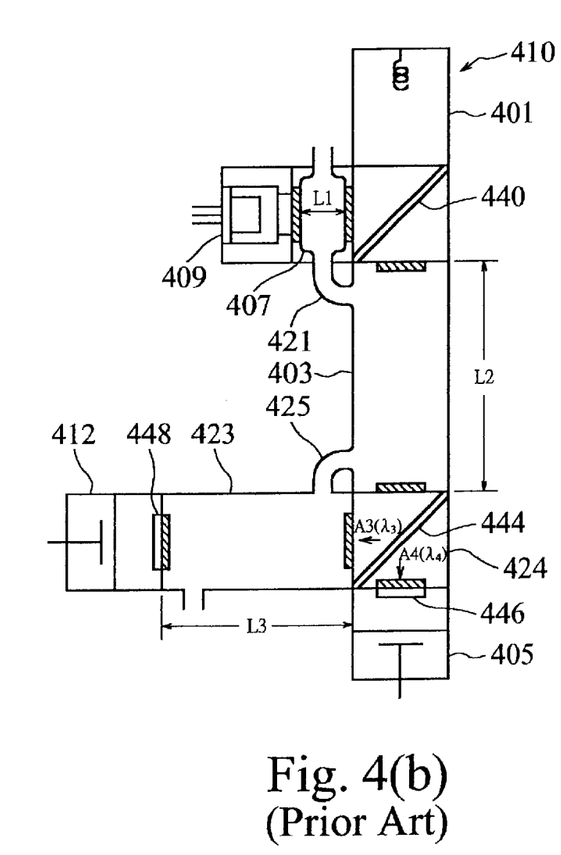

FIG. 4(b) is a gas analyzer of another embodiment of the third prior art disclosed by the same U.S. Pat. No. 5,773,828. As shown in FIG. 4(b), another filter 444 provided between the gas measuring cell 403 and the $NO_x$ detector 405 is also employed to spectrally diffracting another specific wave length of IR. The IR A2, transmitted through the band pass filter 440 and with its specific wave length $\lambda 4$, further transmits through a band pass filter 444 to become A4, and with its another wave length $\lambda 3$, reflects from the band pass filter 444 to become A3. A $NO_x$ detector 405 is provided at an end of the gas measuring cell 403 while a $CO_2$ detector 412 is provided at an end of the gas measuring cell 423. By the use of this apparatus, two different gases $NO_x$ and $CO_2$ can be measured by the two mutually connected gas measuring cells 403 and 423, which have different lengths L2 and L2+L3 respectively, through a communication part 425.

Figure 4C:
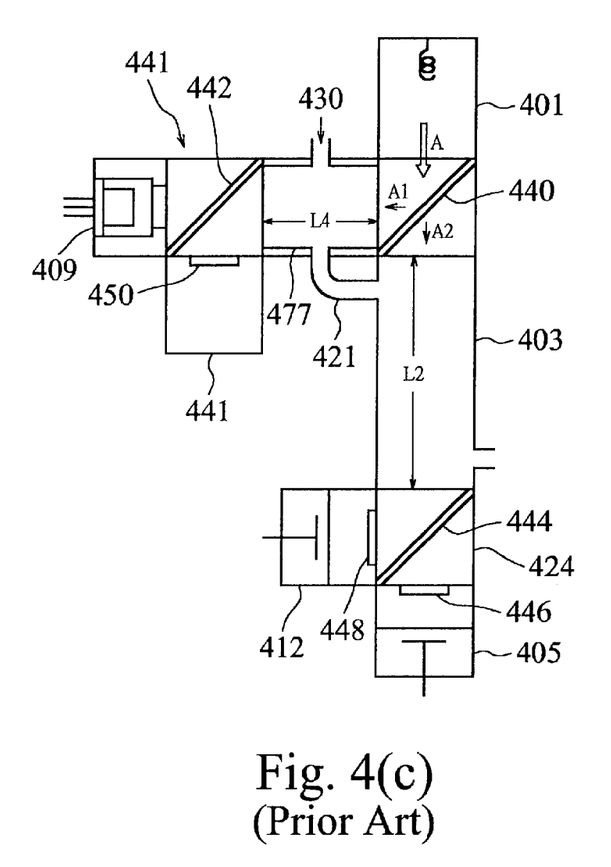

FIG. 4(c) is a gas analyzer of one further embodiment of the third prior art disclosed by the same U.S. Pat. No. 5,773,828. As shown in FIG. 4(c), another gas measuring cell 477 having length L4 is added to the gas measuring cell 403 as shown in FIG. 4(a) in order to add another function for measuring CO gas component. A band pass filter 442 and a CO gas detector 441 are provided at an end of the gas measuring cell 477.

Although the third prior art as mentioned above can match appropriate light path length in accordance with the concentration of the gas components intended to measure, there are still some points of imperfections that are listed as follows 1. The extension of the light path length and the flowing of the gases lack of systematic scheme, thereby, the extension of the gas measuring cells and the set-up of the communication parts grow wild with a lot of branches. Consequently, not only that the apparatus occupies a lot of spaces but the gas flowing through the apparatus is not uniformly distributed also.
2. The proportion of beam-splitting is a fixed one and is unable to be flexibly adjusted, as a result, the light intensity is attenuated after the light path is extended.

SUMMARY OF THE INVENTION

In the light of the disadvantages of the above-mentioned prior arts, one of objectives of the invention is to provide a cassette-type light path system with systematic scheme. The cassette-type light path system can systematically stack up the cassette-type of light absorption chambers to match with appropriate length of light path in accordance with the concentration of the gases intended to measure. This cassette-type light path system of the invention, being not only compact in structural design but also neat, tidy, and good order in shape, is able to save a lot of space, to become portable, and easy to manufacture, thereby, can lower the manufacturing cost.

Another objective of the invention is to provide an integrated light-absorption chamber of cassette-type guided-flow gas. By the use of a plurality of vent hole sets provided on both sides of each of the stacked cassettes, the gases to be analyzed can pass through the cassettes smoothly.

One other objective of the invention is provide a semi-hollow beam splitter in an optical folding system that can adjust the beam splitting proportion effectively. The transmitting beam component in the conventional technology is replaced by a direct method in the invention to have the IR light pass directly through the hollow portion of the beam splitter. In this way, the rate of attenuation of the light intensity is greatly reduced. The proportion of beam splitting is achieved by adjusting the proportion of the hollow portion and the reflective portion. Consequently, the light intensity after beam splitting is maintained in a rational range through adjusting each of the cassette type optical absorption chamber by the adjustment of the beam-splitting proportion.

In order to achieve the above-mentioned objectives, the invention provides a multi-component gas analyzer having a light source system, a cassette-type light path system, an optical folding system, and an infrared detecting system. The light source V system has an infrared light source and a reflector for providing a parallel infrared light beam. The cassette-type light path system has a cassette, an optical absorption chamber, and a set of concave mirrors. A vent hole set having a plurality of vent holes enclosed by an O-ring for sealing the gas between the stacked-up cassettes is provided on the surfaces of the cassette and is disposed in staggered pattern so as to uniformly distribute the gas introduced. An inlet and an outlet for inputting and outputting the parallel infrared light beam are also provided at the cassette. The optical absorption chamber having a highly reflective coating film coated on the inner wall surface thereof is employed for introducing the gases to be tested and providing the space for contact between the gases and the parallel infrared light beam. A set of reflective concave mirrors disposed in staggered pattern on the two opposite sides therein is provided in the optical absorption chamber for guiding the parallel infrared light beam and extending the light path. The optical folding system includes a beam splitter for splitting and distributing the infrared light beam into each of the cassette, and a deflector for guiding infrared light beam to transmit into the next cassette. Finally, the infrared detecting system includes a reference detector and a measuring detector wherein each detector has a filter and a sensor. The filter in the reference detector is distinct from the one in the measuring detector for sensing infrared in closed but distinct frequencies while the sensors in both detectors are exactly the same.

Regarding the invention's object, advantages and characteristics as above-mentioned or others can be better understood by the following"detailed description of the preferred embodiments".

DETAIL DESCRIPTION OF THE PREFERRED EMBODIMENTS

Figure 5:
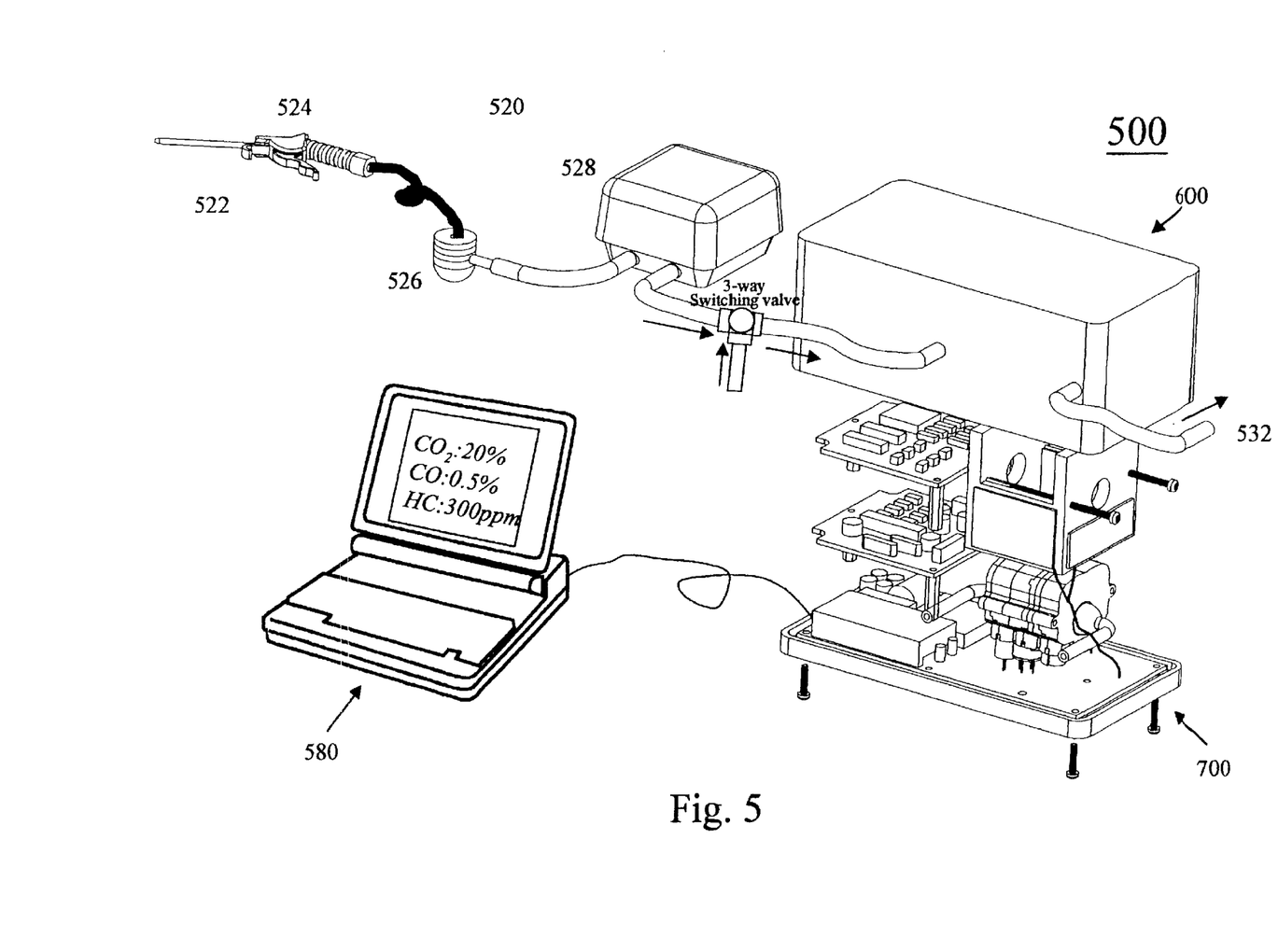
FIG. 5 is a pictorial view of the multi-component gas analyzer module having a cassette-type light-path system of the invention.

FIG. 5 is a pictorial view of the multi-component gas analyzer module having a cassette-type light path system of the invention. As shown in FIG. 5, the multi-component gas analyzer module having cassette-type light path system includes a pretreatment system 520, a gas analyzing main body 600, a signal processing system 700, and a data processing system 580.

The pretreatment system 520 includes a gas inlet 522, a sampling probe 524, a filter 526 with a filtering piece (not shown), a pump 528, and a vent 532. The pretreatment system 520 uses the pump 528 to absorb gases to be analyzed, and uses the sampling probe to perform sampling, adjust temperature and humidity. It also uses the filter 526 to perform filtering to the particles suspended in the gases. The data processing system 540 is employed for analyzing and operating data sent from the signal processing system 700, and displaying results.

Figure 6A:
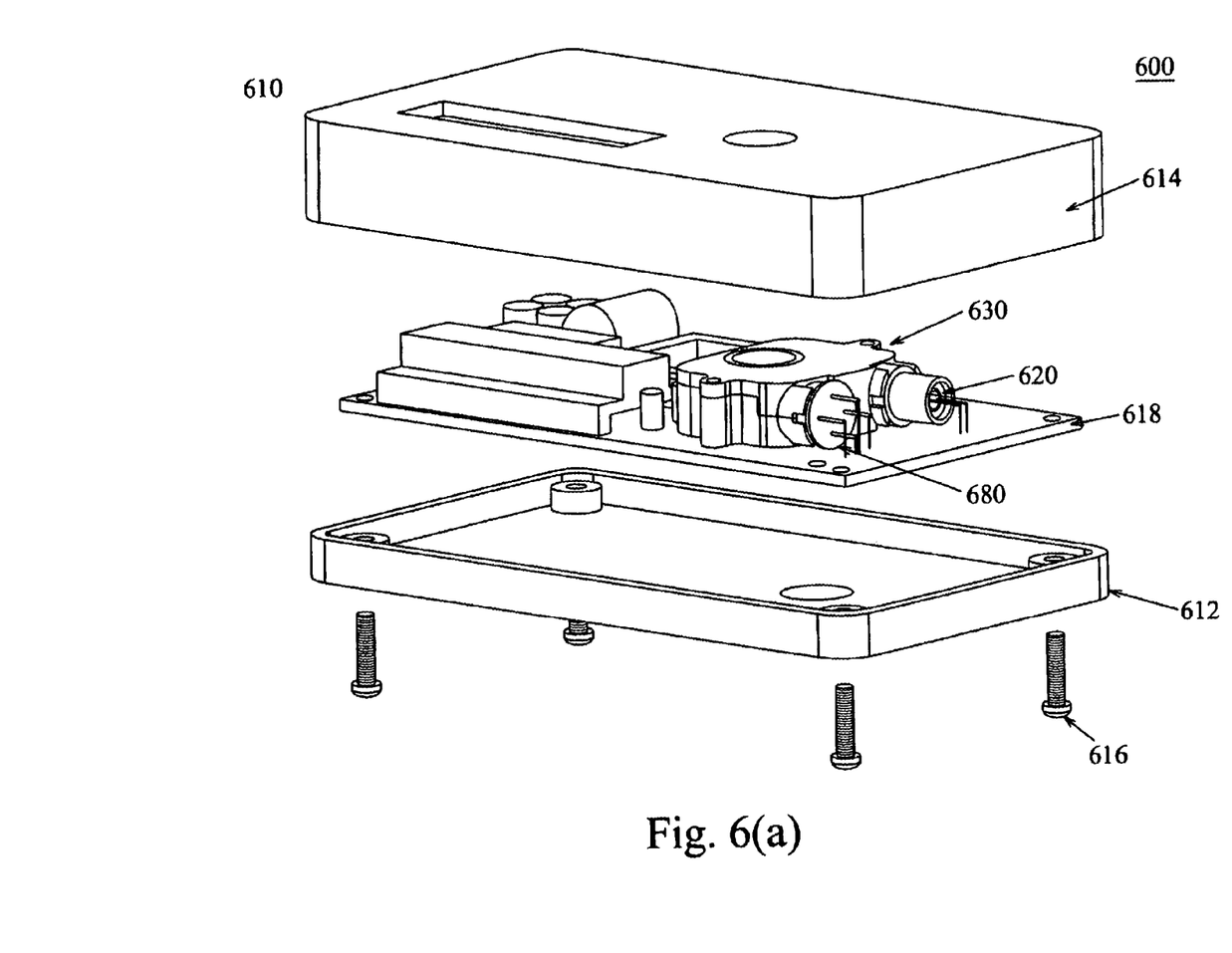
FIG. 6(a) is a pictorial view of the structure of the multi-gas analyzer of the invention.

FIG. 6(a) is a pictorial view of the structure of the multi-gas analyzer of the invention. As shown in FIG. 6(a), the gas analyzing main body 600 for analyzing the gases after being treated by the pretreatment system 520 includes a housing 610, a light source system 620, a light path system 630, an optical folding system (not shown), and an IR detecting system 680. The housing 610 includes a chassis 612, an upper cap 614, a locking member 616, and a substrate 618.

Figure 6B:
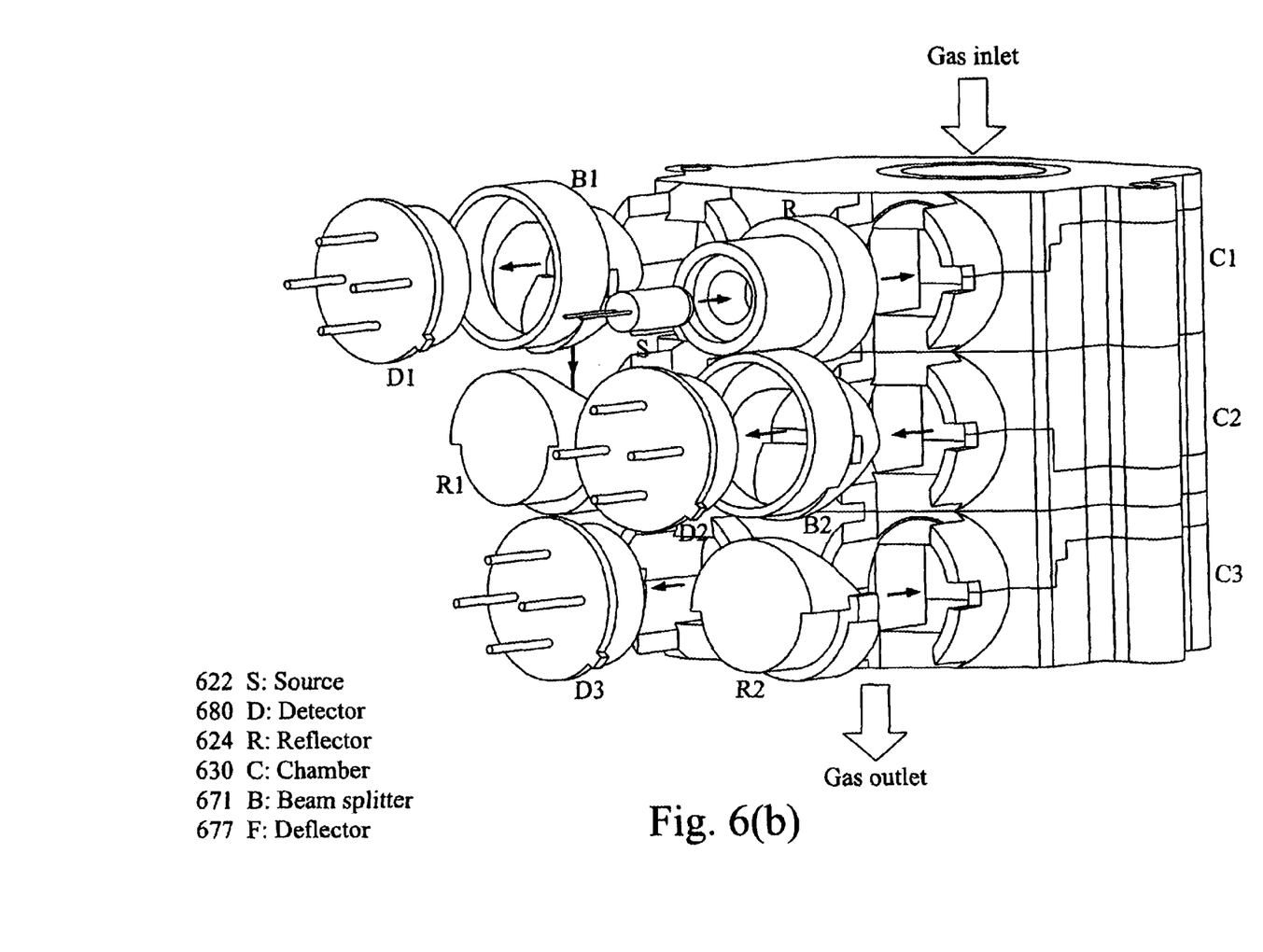
FIG. 6(b) is a pictorial view of the internal structure and the functional operation of the multi-gas analyzer of the invention.

FIG. 6(b) is a pictorial view of the internal structure and the functional operation of the multi-gas analyzer of the invention. As shown in FIG. 6(b), the multi-gas analyzer of the invention includes the light source system having an IR light source 622 (S) and a light-converging parabolic reflector 624 (R), three detectors 680 (D1, D2, D3), two deflectors 677 (F1, F2), three cassettes 640 (C1, C2, C3), and two beam splitters 671 (B1, B2).

Figure 7A:
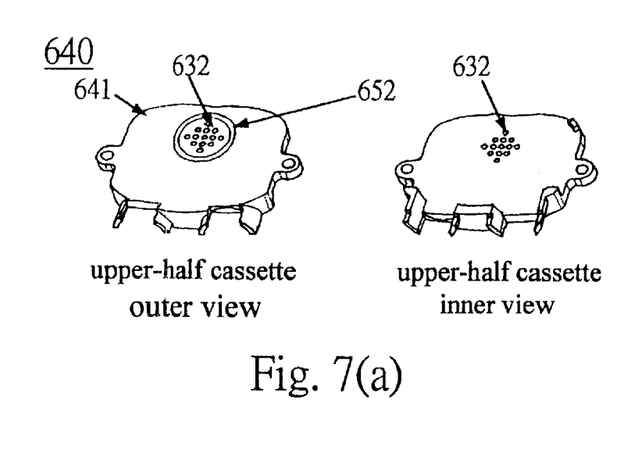
FIGS. 7(a), 7(b) and 7(c) are pictorial views of the internal cassette structure of the multi-gas analyzer of the invention.
Figure 7B:
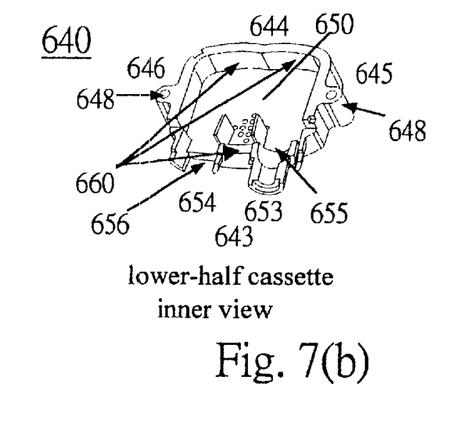
Figure 7C:
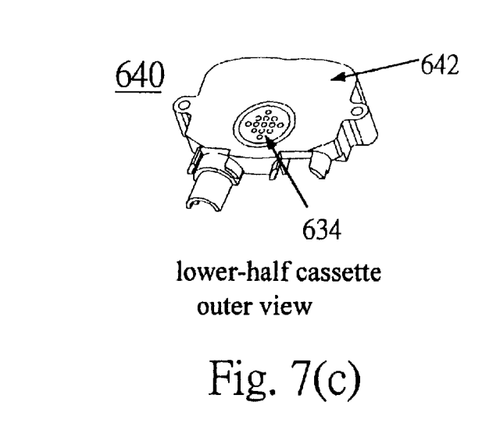

FIGS. 7(a), 7(b) and 7(c) are pictorial views of the internal cassette structure of the multi-gas analyzer of the invention. As shown in FIGS. 7(a), 7(b) and 7(c), the light path system 630 includes a cassette 640, an optical absorption chamber 650, and a set of concave mirror 660. Among them, the cassette 640 has a first surface 641, a second surface 642, a first side 643, a second side 644, a third side 645, and a fourth side 646. A plurality of vent hole sets 632 are provided in the cassette 640 disposed alternately on the opposite surfaces of the first surface 641 and the second surface 642. The vent hole sets are enclosed by O-rings 652 for sealing the gases between the stacked-up cassettes. These vent hole sets 632 and 634 are used to uniformly distribute the gas components to be analyzed.

The first side 643 has a first section 653 and a second section 654. An inlet 655 for inputting the IR light is provided in the first section 653 of the first side 643, while an outlet 656 for outputting the IR light is provided in the second section 654 of the first side 643. The optical absorption chamber 650 is employed to guide the gas components to be analyzed and provide the gas components with space for extending the light path. Besides, several screw bosses 648 for tightening the cassettes are provided respectively on the first side 643, the second side 644, the third side 645, and the fourth side 646. Also, the inner wall of the optical absorption chamber is spread with highly reflective coating.

Figure 8A:
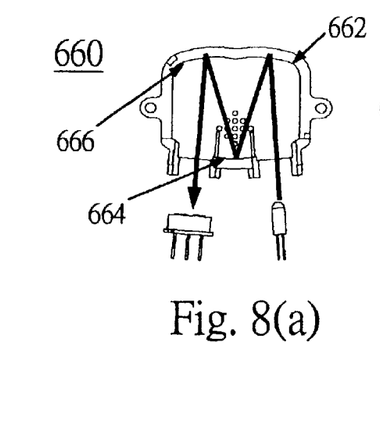
FIGS. 8(a), 8(b) show the top and the bottom views respectively of the internal cassette structure and the light-path of the multi-gas analyzer of the invention.
Figure 8B:
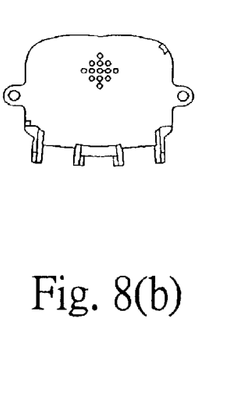

FIGS. 8(a), 8(b) show the top and the bottom views respectively of the internal cassette structure and the light-path of the multi-gas analyzer of the invention. As shown in FIG. 8(a), the concave mirror set 660 includes a first concave mirror 662, a second concave mirror 664, and a third concave mirror 666. These concave mirrors 662, 664, and 666 are alternately disposed in opposite sides 643 (the first side) and 644 (the second side) of the cassette 640. This concave mirror set is for guiding and extending the light path of IR light and providing the output parallel light beam of IR light.

Figure 9:
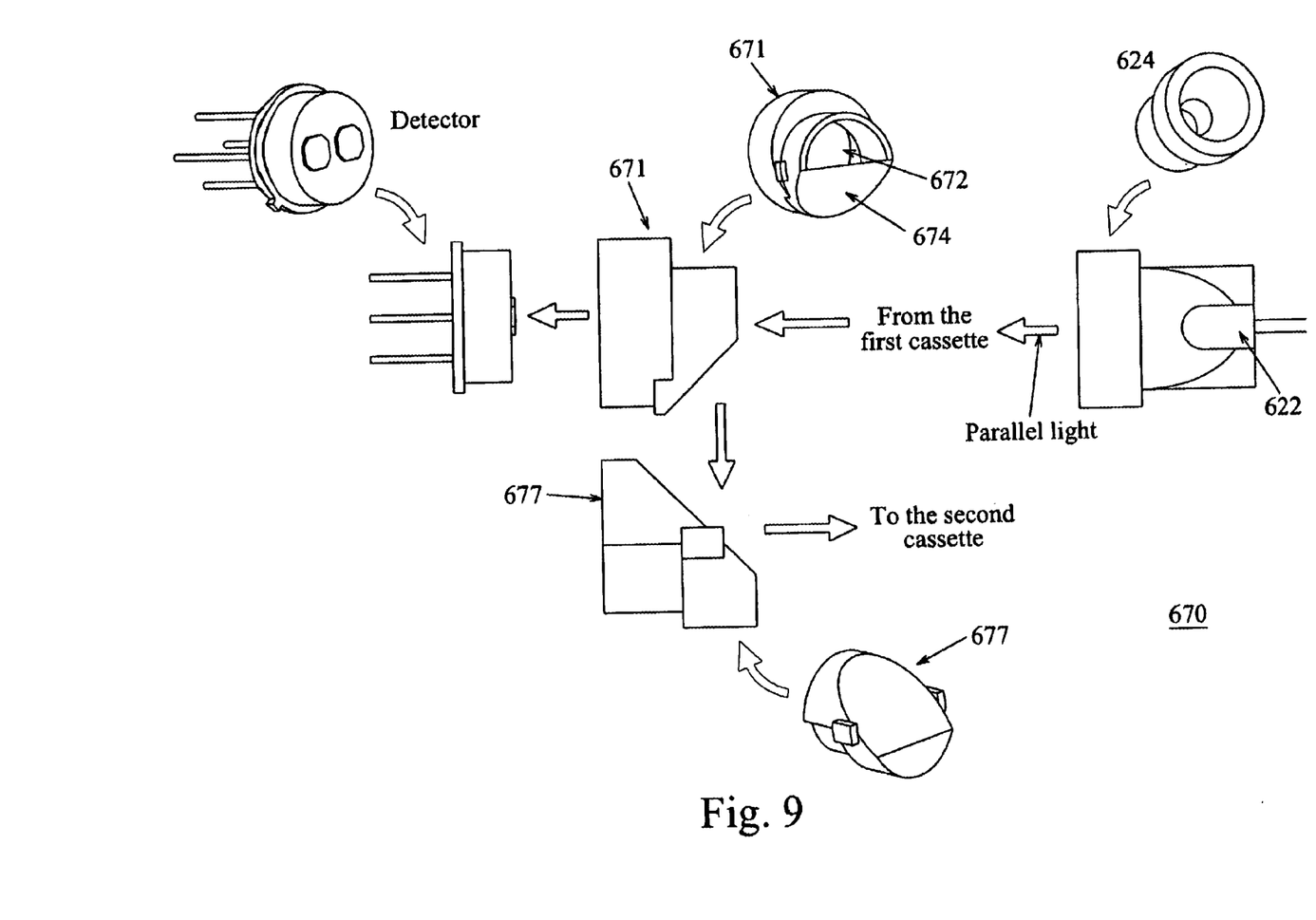
FIG. 9 is a schematic function diagram of the optical folding system in the multi-gas analyzer of the invention.

FIG. 9 is a schematic function diagram of the optical folding system in the multi-gas analyzer of the invention. As shown in FIG. 9, the optical folding system 670 includes a beam splitter 671 and a deflector 677 where all the surfaces through which the light path passes are all spread with highly reflective coating. Also, the deflector 677 is employed to guide the IR light to transmit from one cassette to others. Moreover, the beam splitter 671, being a semi-hollow type of beam splitter, has its mirror with a hollow portion 672 and a reflective mirror portion 674. The proportion of beam splitting is determined by the ratio of the area of the hollow portion and the reflective mirror portion.

Figure 10:
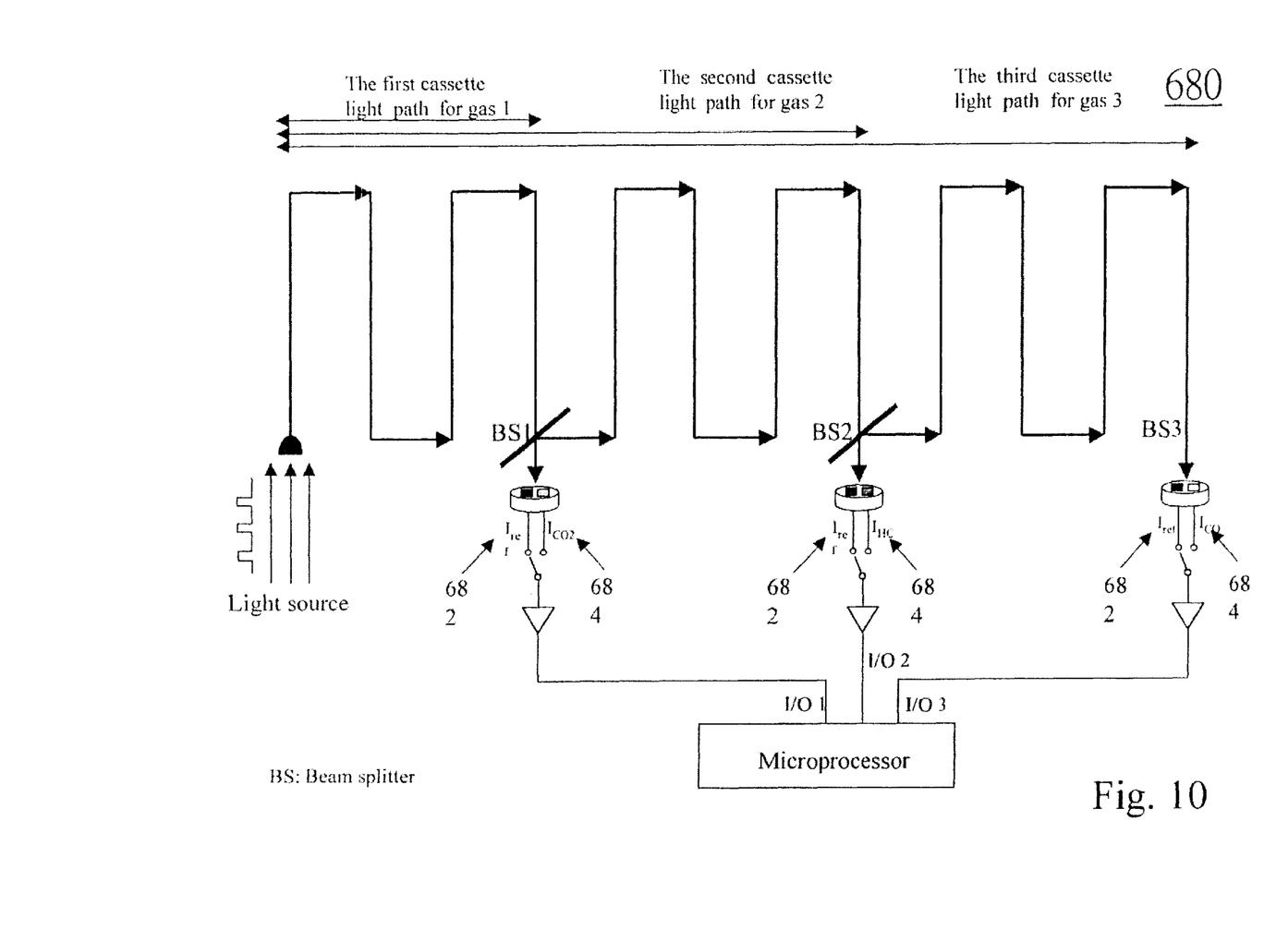
FIG. 10 is a schematic function diagram of the dual channel detector of the infrared detecting system in the multi-gas analyzer of the invention.

FIG. 10 is a schematic function diagram of the dual channel detector of the infrared detecting system in the multi-gas analyzer of the invention. As shown in FIG. 10, the IR detecting system 680, being a dual channel detector, includes a reference detector 682 and a measuring detector 684 wherein each detector has a filter (not shown) and a sensor (not shown). The filter in the reference detector is distinct from the one in the measuring detector for sensing infrared in closed but distinct frequencies but the sensors 682, and 684 in both detectors are exactly the same.

Figure 11:
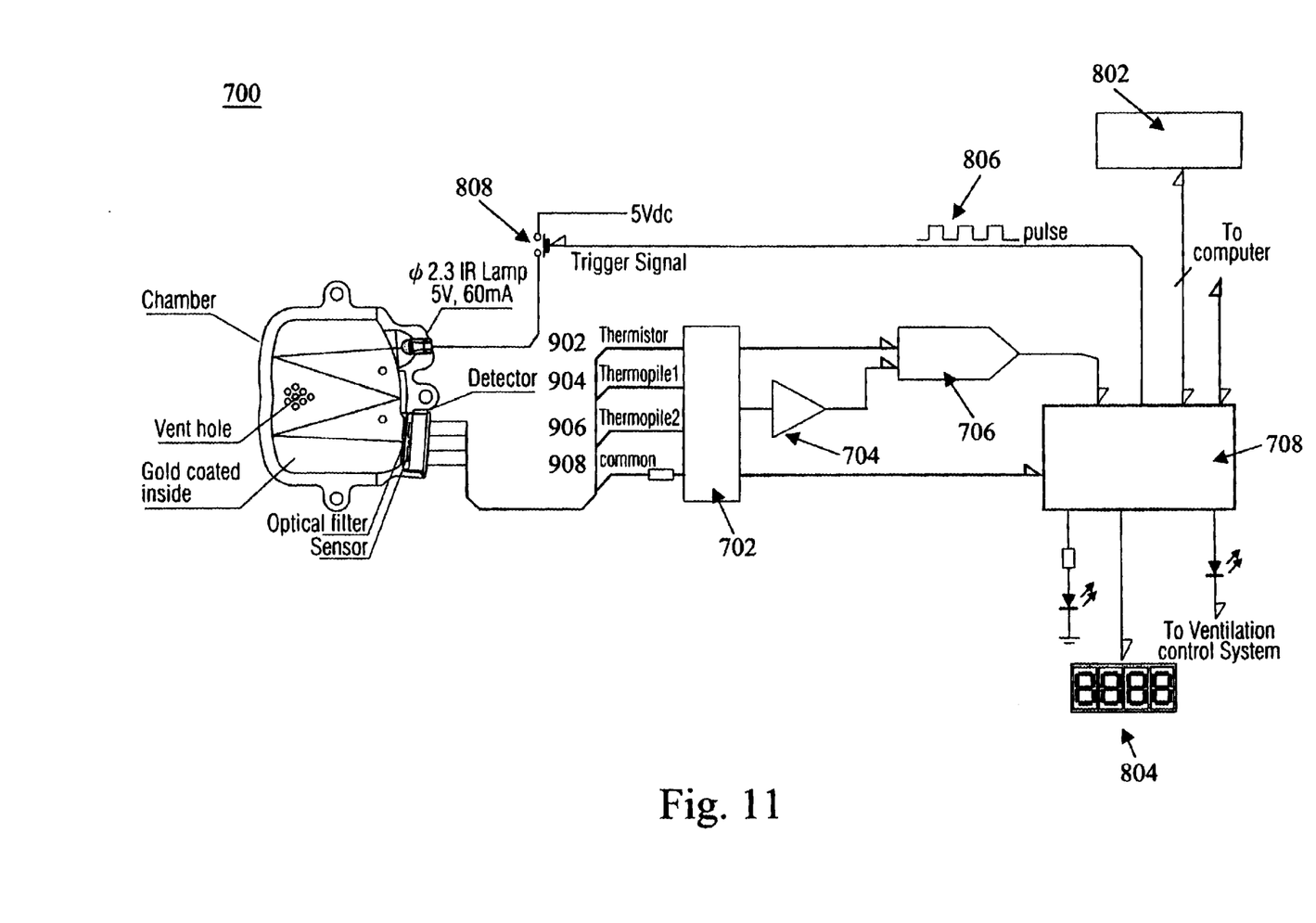
FIG. 11 is a schematic function diagram of the signal processing system in the multi-gas analyzer of the invention.

FIG. 11 is a schematic function diagram of the signal processing system in the multi-gas analyzer of the invention. As shown in FIG. 11, the signal processing system 700 includes an analog multiplexer 702, an amplifier 704, an analog/digital converter (A/D converter) 706, a central processing unit (CPU) 708, an EEPROM (electrical erasable programmable read only memory) memory storage 802, a communication system (not shown), a power supply system (not shown), and a display apparatus 804.

The analog multiplexer 702 is for switching between the reference detector 682 and the measuring detector 684 (see FIG. 10). The amplifier 704 is for amplifying signals, the analog/digital converter (A/D converter) 706 is for converting an analog signal into a digital signal, and the central processing unit (CPU) 708 is for assigning duty, setting up working environment, and executing a portion of mathematical operations. Moreover, the EEPROM memory storage 802 is for saving parameters, the communication system is for transmitting data, and the display system 804 is for displaying results.

The operation principle of the multi-component gas analyzer having cassette type light path system is explained as follows:

As shown in FIG. 5, the gases need to be treated by the pretreatment system 520 before being introduced into the gas analyzer 600. First of all, the gases are sampled by the sampling probe 524, and are introduced by the gas analyzer 600 after the pump 528 is turned on. The impurities such as suspended particles contained in the gases are then removed by performing filtering by the filter 526, and the moisture in the gases is also removed by heating process. Next, the gases, through the treatment of the pretreatment system 500, are guided into the optical absorption chamber 650 of the cassette 640 through the vent hole set 632 on the first surface 641 as shown in FIG. 7(a), FIG. 7(b), and FIG. 7(c). An O-ring 652 is provided to encircle the vent hole sets 632 for preventing the polluted gases from invading the sampled gases. The vent hole set 634 provided on the second surface 642 of the cassette 640 is for letting the gases flow through each of the cassettes 640. The vent hole set 632 on the first surface 641 and the vent hole set 634 on the second surface of the cassette 640 are alternately disposed near the second side 644 and near the first side 643 respectively. The purpose of this kind of disposition is that the gases flowing through the stacked cassettes can be uniformly distributed in the optical absorption chamber 650. The vent hole sets 632 and 634 can be set up at any location in the optical absorption chamber as long as they are out of the way of the light path.

Next, as shown in FIG. 9, the light beam originated from the light source 622 transmits into the beam splitter 671 after converging through the converging parabolic concave mirror 624. A portion of the light beam passes through the hollow part 672 of the beam splitter 671 and is detected by the detector in the first cassette while the other portion of the light beam reflects from the mirror part 674 of the beam splitter 671 toward the deflector 677. The light beam then reflects from the deflector 677, and as shown in FIG. 8(a), transmits into the second cassette 640 and so on to the rest of the cassettes. In each of the cassette, the light beam reflects through the first, the second, and the third concave mirrors 662, 664, and 666 successively.

Again, as shown in FIG. 11, the IR input in the light source system 620 [see FIG. 6(a)] provides a pulse 806 through the control of a micro-processor 708 (or CPU). Through the switching action of a switch 808, the analyzer provides a dark background light as a reference of an off-position to compare with bright light of an on-position so that the accuracy of the analyzer is not affected by the different environmental lights. In addition, a multiplexer 702, being employed to switch the detector's signal, is used for switching to select a thermistor 902 for measuring temperature, a thermopile I 904 and thermopile II 906 for measuring light intensity, as well as a common 908 for measuring differentiation value of the circuit.

In the multi-component gas analyzer having cassette-type light path system, the length of light path of each of the cassette is a constant. Moreover, the lengths of light path of all of the cassettes are the same, and the required length for a gas component to be analyzed determines the number of cassettes needed for the gas analyzer.

In the multi-component gas analyzer having cassette-type light path system, the material of the highly reflective coating is gold (Au), or zinc selenide (ZnSe) or silver (Ag), or aluminum (Al).

In the multi-component gas analyzer having cassette-type light path system, the material of the splitter and the deflector is ABS resin or PC resin.

While the invention has been described by way of example and in terms of a preferred embodiment, it is to be understood that the invention is not limited to the disclose embodiment. On the contrary, it is intended to cover various modifications. Therefore, the scope of the appended claims should be accorded the broadest interpretation so as to encompass all such modifications.

What is claimed is:

1. A gas analyzer comprising:
   a light source system including an infrared light source and a reflector for providing a parallel infrared light beam;
   a cassette-type light path system including a cassette, an optical absorption chamber, and a set of concave mirrors, wherein:
     the cassette includes a first surface, a second surface, a first side having a first section and a second section, a second side, a third side, and a fourth side, and a vent hole set including a plurality of vent holes, alternately disposed on the first surface and the opposite second surface and enclosed by an O-ring that is provided for sealing a gas component contained in the cassette, for uniformly distributing the gas component to be tested, wherein an inlet and an outlet are provided respectively in the first and the second sections of the first side for respectively inputting and outputting the parallel infrared light beam;

the optical absorption chamber is for guiding the gas component to be tested and for providing an extended space for contact between the gas component and the parallel infrared light beam, an inner wall of the optical absorption chamber being coated with a highly reflective coating film; and the set of concave mirrors includes a first concave mirror, a second concave mirror, and a third concave mirror alternately disposed on the first side and the opposite second side for guiding the parallel infrared light beam and extending a light path of the parallel infrared light beam;

an optical folding system including a beam splitter and a deflector for guiding the parallel infrared light beam, wherein each of the beam splitter and the deflector is coated with a highly reflective coating film; and an infrared detecting system including a reference detector and a measuring detector, each of which includes a filter and a sensor, wherein since the filter in the reference detector and the filter in the measuring detector induce infrared light beams having close but distinct frequencies, they are distinct detectors while the sensor in the reference detector and the sensor in the measuring detector are identical.

2. The gas analyzer of claim 1, wherein the beam splitter is of a semi-hollow type having a portion of reflective mirror and another portion of hollow part, and the proportion of beam splitting is in according with the proportion of the hollowing part area and the reflective mirror area.

3. The gas analyzer of claim 1, wherein the material of the splitter is zinc selenide (ZnSe).

4. The gas analyzer of claim 1, wherein the material of the splitter and the deflector is selected from the group consisting of ABS resin and PC resin.

5. The gas analyzer of claim 1, wherein the material of the highly reflective coating film is selected from the group consisting of gold (Au), silver (Ag), and aluminum (Al).

6. The gas analyzer of claim 1, wherein the cassette-type light path system further includes at least one additional cassette stacked up together with the cassette, each of the at least one additional cassette having the same constitution with the cassette.

7. The gas analyzer of claim 1, wherein the disposition of the vent hole set is at any locations not to interfere the light path of the parallel infrared light beam.

8. The gas analyzer of claim 1, wherein a size of the cassette depends on a length of the light path of the parallel infrared light beam required by the gas component to be tested.

9. A gas analyzer module comprising:

a pretreatment system, including a gas inlet, a sampling probe, a filter with a filtering piece, and a pump for absorbing gases to be analyzed, performing sampling, adjusting temperature and humidity, as well as performing filtering to the particles suspended in the gases to be analyzed;

a gas analyzing main body for analyzing the gases after being treated by the pretreatment system, including:

a light source system including an infrared light source and a reflector for providing a parallel infrared light beam;

a cassette-type light path system including a cassette, an optical absorption chamber, and a set of concave mirrors, wherein:

the cassette includes a first surface, a second surface, a first side having a first section and a second section, a second side, a third side, and a fourth side, and a vent hole set including a plurality of vent holes, alternately disposed on the first surface and the opposite second surface and enclosed by an O-ring that is provided for sealing the gases contained in the cassette, for uniformly distributing the gases to be analyzed, wherein an inlet and an outlet are provided respectively in the first and the second sections of the first side for respectively inputting and outputting the parallel infrared light beam;

the optical absorption chamber is for guiding the gases to be analyzed and for providing an extended space for contact between the gas component and the parallel infrared light beam, an inner wall of the optical absorption chamber being coated with a highly reflective coating film; and the set of concave mirrors includes a first concave mirror, a second concave mirror, and a third concave mirror alternately disposed on the first side and the opposite second side for guiding the parallel infrared light beam and extending a light path of the parallel infrared light beam;

an optical folding system including a beam splitter and a deflector for guiding the parallel infrared light beam, wherein each of the beam splitter and the deflector is coated with a highly reflective coating film; and an infrared detecting system including a reference detector and a measuring detector, each of which includes a filter and a sensor, wherein since the filter in the reference detector and the filter in the measuring detector induce infrared light beams having close but distinct frequencies, they are distinct detectors while the sensor in the reference detector and the sensor in the measuring detector are identical;

a signal processing system including an analog multiplexer for switching between the reference detector and the measuring detector, an amplifier for amplifying signals, an analog/digital converter (A/D converter) for converting an analog signal into a digital signal, a central processing unit (CPU) for assigning duty, setting up working environment, and executing a portion of mathematical operations, a memory storage for saving parameters, a communication system for transmitting data, as well as a display system for displaying results; and a data processing system for processing data sent from the signal processing system wherein the processing jobs including analyzing, operating data, and displaying results.

10. The gas analyzer module of claim 9, wherein the cassette-type light path system further includes at least one additional cassette stacked up together with the cassette, each of the at least one additional cassette having the same constitution with the cassette.

11. The gas analyzer module of claim 9, wherein the beam splitter is of a semi-hollow type having a portion of reflective mirror and another portion of hollow part, and the proportion of beam splitting is in according with the proportion of the hollowing part area and the reflective mirror area.

12. The gas analyzer module of claim 9, wherein the material of the highly reflective coating film is selected from the group consisting of gold (Au), silver (Ag), and aluminum (Al).

13. The gas analyzer module of claim 9, wherein the material of the splitter is a zinc selenide (ZnSe).

14. The gas analyzer module of claim 9, wherein the material of the splitter and the deflector is selected from the group consisting of ABS resin and PC resin.

15. The gas analyzer module of claim 9, wherein the disposition of the vent hole set is at any locations not to interfere the light path of the parallel infrared light beam.

16. The gas analyzer module of claim 9, wherein a size of the cassette depends on a length of the light path of the parallel infrared light beam required by the gases to be analyzed.

* * * * *